United States Patent
Park et al.

(10) Patent No.: US 7,424,091 B2
(45) Date of Patent: Sep. 9, 2008

(54) COMBINED PANORAMIC, CT (COMPUTED TOMOGRAPHY) AND CEPHALOMETRIC PHOTOGRAPHING APPARATUS

(75) Inventors: Jae-Yoon Park, Hwaseong Si (KR); Young-Gyun Jin, Suwon Si (KR); Tae-Woo Kim, Hwaseong Si (KR)

(73) Assignees: E-Woo Technology Co., Ltd., Yongin-Si (KR); Vatech Co., Ltd., Hwaseong-Si (KR)

( * ) Notice: Subject to any disclaimer, the term of this patent is extended or adjusted under 35 U.S.C. 154(b) by 37 days.

(21) Appl. No.: 11/298,857

(22) Filed: Dec. 9, 2005

(65) Prior Publication Data

US 2007/0030951 A1 Feb. 8, 2007

(30) Foreign Application Priority Data

Aug. 8, 2005 (KR) ...................... 10-2005-0072180

(51) Int. Cl.
*A61B 6/14* (2006.01)
(52) U.S. Cl. ........................................ 378/39
(58) Field of Classification Search ............. 378/38–40, 378/168, 193, 195, 196, 197
See application file for complete search history.

(56) References Cited

U.S. PATENT DOCUMENTS

| | | | | |
|---|---|---|---|---|
| 6,118,842 | A | 9/2000 | Arai et al. | 378/39 |
| 6,829,326 | B2 | 12/2004 | Woods et al. | 378/38 |
| 7,236,563 | B2 * | 6/2007 | Sa et al. | 378/39 |
| 7,315,608 | B2 * | 1/2008 | Sa et al. | 378/38 |
| 2001/0036246 | A1 * | 11/2001 | Graumann | 378/39 |
| 2004/0190678 | A1 * | 9/2004 | Rotondo et al. | 378/38 |

* cited by examiner

*Primary Examiner*—Courtney Thomas
(74) *Attorney, Agent, or Firm*—John K. Park; Park Law Firm

(57) ABSTRACT

Disclosed herein is a combined panoramic, CT (Computed Tomography) and cephalometric photographing apparatus including: a base; a supporting pole; an elevation member; a panoramic and CT photographing part; and a cephalometric photographing part. The panoramic and CT photographing part includes: a rotary arm supporting member; a rotary arm arranging an X-ray source part and an X-ray sensor part in such a way that the X-ray source part and the X-ray sensor part are opposed to each other, the X-ray sensor part having a panoramic sensor and/or a CT sensor; and rotary arm driving means. A distance between the X-ray source part and the X-ray sensor part arranged opposed to each other with respect to the rotary arm is variable. The apparatus can conduct all of panoramic photographing, CT photographing and cephalometric photographing, and provide the optimum enlargement ratio according to whether the panoramic photographing or the CT photographing is conducted.

25 Claims, 10 Drawing Sheets

COMBINED PANORAMIC, CT (COMPUTED TOMOGRAPHY) AND CEPHALOMETRIC PHOTOGRAPHING APPARATUS

TECHNICAL FIELD

The present invention relates to a combined panoramic, CT (Computed Tomography) and cephalometric photographing apparatus, more particularly, to a combined panoramic, computed tomography and cephalometric photographing apparatus, which can vary a distance between an X-ray source part and an X-ray sensor part arranged on a rotary arm and opposed to each other.

BACKGROUND ART

In the field of the medical diagnosis, conventionally, an X-ray CT (Computerized Tomography) imaging apparatus is a photographing apparatus in which an X-ray beam of a predetermined amount is transmitted to a patient's site to be imaged or photographed, the transmitted X-ray amount is measured by an X-ray sensor and the measured data is recorded in a memory, and an X-ray absorbing rate of each point of the captured bodily region of the patient is obtained by a computer and is reconstructed into an image. In the field of the dental diagnosis, an X-ray panoramic photographing apparatus is an apparatus for conducting tomography while rotating along a locus suitable for the form of a dental arch. A cephalometric imaging apparatus is a photographing apparatus which is mainly used for corrective orthodontics or orthognatic surgery, and is to take a photograph of a patient's head.

The conventional X-ray CT photographing apparatus can obtain only a CT image, and the conventional panoramic photographing apparatus can obtain only a photographic image. Therefore, recently, combined panoramic and computed tomography photographing apparatuses have been proposed.

U.S. Pat. No. 6,118,842 discloses an X-ray imaging apparatus which can conduct both the CT imaging and the panoramic imaging. The apparatus includes: an X-ray source for generating X-rays, an X-ray sensor for detecting X-rays having passed through an object, and supporting means for supporting the X-ray source and the X-ray sensor so that the X-ray source and the X-ray sensor are opposed to each other across an object; and mode switching means for switching between a CT mode and a panorama mode. To detect X-rays, only one X-ray sensor is used, and the X-ray sensor is an area sensor which is capable to detect a large area. The X-ray imaging apparatus can obtain the tomography image by converting the photographic mode into the panoramic mode after obtaining the CT image by selecting the CT mode.

Furthermore, various X-ray photographing apparatus for conducting not only panoramic photographing but also cephalometric photographing have been disclosed.

U.S. Pat. No. 6,829,326 discloses a combined panoramic and cephalometric photographing apparatus. When cephalometric photographing is conducted after panoramic photographing, the apparatus conducts the cephalometric photographing after properly moving a collimator so that a panoramic sensor does not detect X-rays generated from an X-ray source.

However, the conventional imaging apparatus conducts the CT photographing and the panoramic photographing using only one sensor, and hence, needs an expensive sensor capable of carrying out the two photographing functions. Additionally, the conventional imaging apparatus has another problem in that it is difficult to obtain the optimum image according to the CT photographing or the panoramic photographing since a distance between the X-ray sensor and the X-ray source is uniform.

DISCLOSURE OF INVENTION

Technical Problem

Accordingly, it is an object of the present invention to provide a combined panoramic, CT (Computed Tomography) and cephalometric photographing apparatus, which can obtain a CT image, a tomographic image and a cephalometric image by using a CT sensor, a panoramic sensor and a cephalometric sensor mounted in one photographing apparatus, and which can apply the optimum enlargement ratio according to panoramic photographing or CT photographing.

Technical Solution

To achieve the above object, the present invention provides a combined panoramic, CT (Computed Tomography) and cephalometric photographing apparatus. The combined panoramic, CT and cephalometric photographing apparatus includes: a base; a supporting pole standing on the base; an elevation member mounted on the supporting pole in such a way as to elevate and displace in a vertical direction; a panoramic and CT photographing part mounted on the front surface of the elevation member; and a cephalometric photographing part connected to a side of the elevation member, wherein the panoramic and CT photographing part includes: a rotary arm supporting member connected to the front upper portion of the elevation member; a rotary arm supported by the rotary arm supporting member and arranging the X-ray source part for generating X-rays and the X-ray sensor part thereon in such a way that the X-ray source part and the X-ray sensor part are opposed to each other, the X-ray sensor part having a panoramic sensor and/or a CT sensor for detecting X-rays which are generated from the X-ray source part and pass through an object; and rotary arm driving means interposed between the rotary arm and the rotary arm supporting member for driving the rotary arm, and wherein a distance between the X-ray source part and the X-ray sensor part opposed to each other on the rotary arm is variable.

The combined panoramic, CT and cephalometric photographing apparatus further includes X-ray source part driving means mounted at a location where the rotary arm and the X-ray source part are connected with each other. The X-ray sensor part is fixed on the rotary arm, and the X-ray source part is horizontally moved in a direction to get near to the X-ray sensor part or in a direction to get away from the X-ray sensor part without regard to the rotary arm.

The combined panoramic, CT and cephalometric photographing apparatus further includes X-ray source part driving means mounted at a location where the rotary arm and the X-ray source part are connected with each other, and X-ray sensor part driving means located at a location where the rotary arm and the X-ray sensor part are connected with each other. The X-ray sensor part is rotated without regard to the rotary arm, and the X-ray source part is horizontally moved in a direction to get near to the X-ray sensor part or in a direction to get away from the X-ray sensor part without regard to the rotary arm.

The combined panoramic, CT and cephalometric photographing apparatus further includes X-ray sensor part driving means mounted at a location where the rotary arm and the X-ray sensor part are connected with each other. The X-ray sensor part is rotated without regard to the rotary arm, and the X-ray source part is fixed on the rotary arm.

ADVANTAGEOUS EFFECTS

The combined panoramic and computed tomography photographing apparatus according to the present invention provides an effect to take all of a CT image, a panoramic image and a cephalometric image by mount a CT sensor, a panoramic sensor and a cephalometric sensor on one photographing apparatus. Furthermore, the present invention allows the user to take an image in the optimum enlargement ratio according to whether the panoramic photographing or the CT photographing is conducted, by varying and regulating a distance between the X-ray source part and the X-ray sensor part.

Moreover, conventionally, only one expensive X-ray sensor for conducting both of the panoramic photographing and the CT photographing has been used. However, the present invention uses a dedicated X-ray sensor for panoramic photographing and a dedicated X-ray sensor for CT photographing, thereby reducing costs.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

Figure 1:
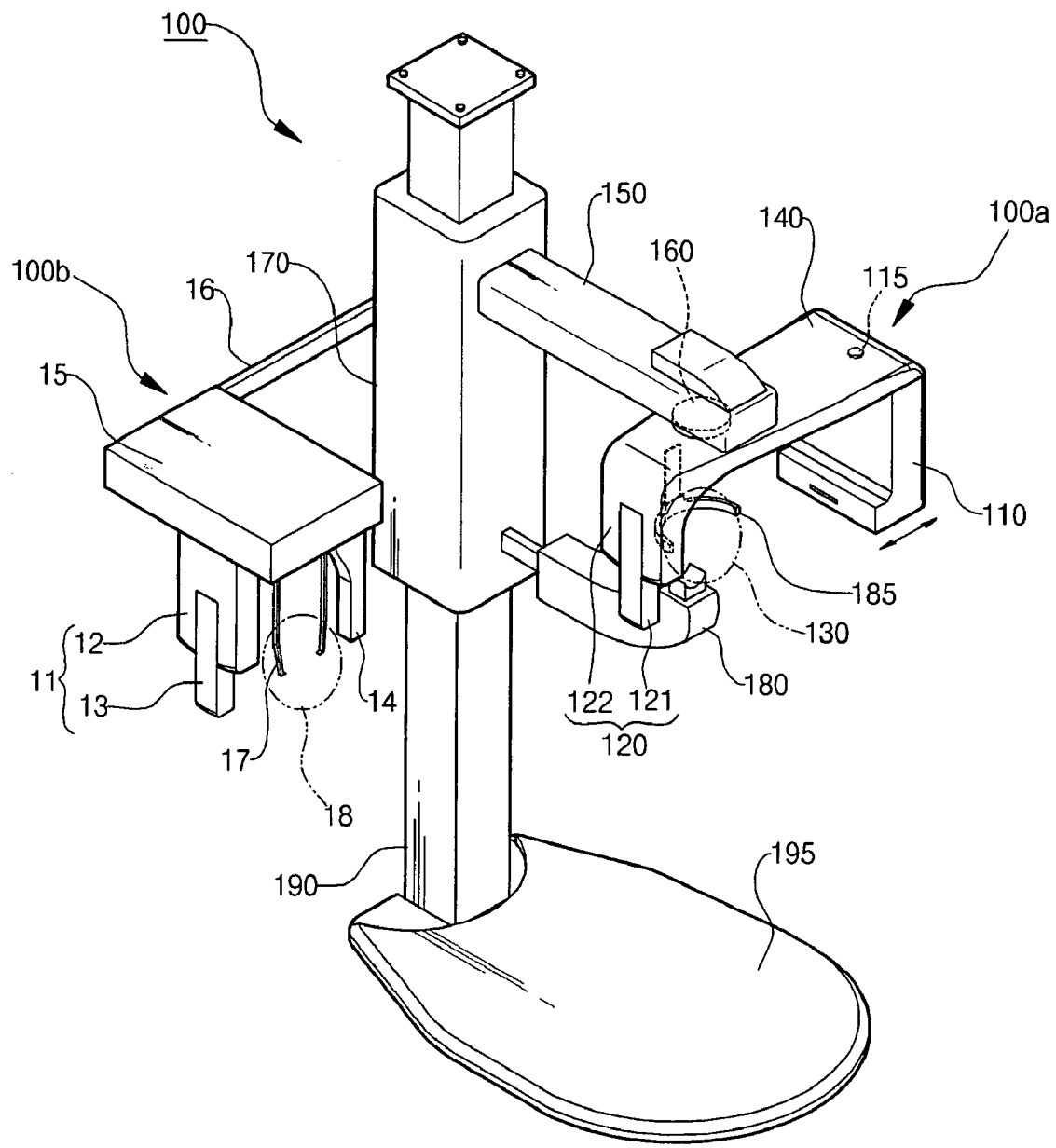
FIG. 1 is a perspective view of a combined panoramic, computed tomography and cephalometric photographing apparatus according to a first preferred embodiment of the present invention.

EXPLANATION ON ESSENTIAL REFERENCE NUMERALS IN DRAWINGS 100,200,300,400: combined panoramic, CT and cephalometric photographing apparatus
100a,200a,300a,400a: panoramic and CT photographing part
100b,200b,300b,400b: cephalometric photographing part
110,210,310,410: X-ray source part
120,220,320,420: X-ray sensor part
221,321, 421: panoramic sensor
223,323,423: CT sensor
115,215,315: X-ray source part driving means
325: X-ray sensor part driving means
140,240,340,440: rotary arm
150: rotary arm supporting member
160: rotary arm driving means
170: elevation member
180: chin supporting member
11: cephalometric sensor part
12: cephalometric sensor mounting part
13: cephalometric sensor
14: collimator

BEST MODE

Reference will now be made in detail to the preferred embodiments of the present invention, examples of which are illustrated in the accompanying drawings. The present invention is not restricted to the embodiments of the present invention but can be embodied in other various forms. The same reference numerals designate the same parts in the present invention.

FIG. 1 is a perspective view of a combined panoramic, CT (Computed Tomography) and cephalometric photographing apparatus according to a first preferred embodiment of the present invention, and FIGS. 2 to 5 are front views for showing an operation of an X-ray source part of the combined panoramic, computed tomography and cephalometric photographing apparatus according to the first preferred embodiment of the present invention.

Referring to FIG. 1, the combined panoramic, computed tomography and cephalometric photographing apparatus 100 includes a base 195, a supporting pole 190, an elevation member 170, a panoramic and CT photographing part 100a, and a cephalometric photographing part 100b, and can conduct CT photographing, panoramic photographing, and cephalometric photographing.

The base 195 supports the supporting pole 190 on which the above components are mounted, and the supporting pole 190 stands and is mounted at a side of the base 195.

The elevation member 170 is mounted on the supporting pole 190. The elevation member 170 includes a control motor for allowing a vertical displacement. Therefore, the apparatus 100 can regulate its own height according to a patient's height.

The panoramic and CT photographing part 100a is mounted on the front surface of the elevation member 170, and the cephalometric photographing part 100b is connected to a side of the elevation member 170.

The panoramic and CT photographing part 100a will be described in detail. The panoramic and CT photographing part 100a includes: a rotary arm supporting member 150 connected to the front upper portion of the elevation member 170; a rotary arm 140 supported by the rotary arm supporting member 150 and arranging the X-ray source part 110 for generating X-rays and the X-ray sensor part 120 thereon in such a way that the X-ray source part 110 and the X-ray sensor part 120 are opposed to each other; and rotary arm driving means 160 interposed between the rotary arm 140 and the rotary arm supporting member 150 for driving the rotary arm 140.

A chin supporting member 180 is mounted at the lower portion of the elevation member 170 in nearly orthogonal direction to the elevation member 170. The chin supporting member 180 is formed to position the patient's chin thereon. At this time, the patient's head is located between the X-ray sensor part 120 and the X-ray source part 110 disposed on the rotary arm 140. The chin supporting member 180 can be driven without regard to driving of the elevation member 170.

The rotary arm supporting member 150 is mounted at the upper portion of the elevation member 170 in nearly orthogonal direction to the elevation member 170. The rotary arm supporting member 150 supports the rotary arm 140 by the rotary arm driving means 160. The rotary arm supporting member 150 has lines (not shown) formed to allow movement of the rotary arm driving means 160, so that the rotary arm driving means 160 can move along the lines.

The rotary arm driving means 160 moves in a direction that the rotary arm supporting member 150 is connected to the elevation member 170 (X-axis movement), and in a horizontal direction which is orthogonal to the X-axis movement direction (X-axis movement). Furthermore, the rotary arm driving means 160 can be rotated on a central axis. That is, the rotary arm driving means 160 conducts the CT photographing or the panoramic photographing by driving the rotary arm 140. In case of the CT photographing, the rotary arm driving means 160 rotates the rotary arm 140 on the central axis in order to conduct photographing, and in case of the panoramic photographing, the rotary arm driving means 160 drives the rotary arm 140 on the X-axis and the Y-axis and drives the rotary arm 140 rotationally in order to conduct photographing. The rotary arm supporting member 150 and the elevation member 170 respectively includes mechanical components, such as a control motor, therein which are necessary for driving of the rotary arm driving means 160, and a rotary arm driving means controller for controlling the rotary arm driving means 160 to move the rotary arm 140 along the fixed locus according to the CT photographing or the panoramic photographing. The mechanical function will not be described since it is clear to those skilled in the art.

The X-ray source part 110 is connected to an end of the rotary arm 140, and the X-ray sensor part 120 is connected to the other end of the rotary arm 140. The X-ray sensor part 120 and the X-ray source part 110 are opposed to each other.

The X-ray source part 110 emits and irradiates X-rays to a patient 130 or an object. The X-ray source part 110 includes an X-ray source and a collimator, so that the emitted X-rays pass through the object and are irradiated to the X-ray sensor part 120.

The X-ray source part 110 can be driven without regard to the driving of the rotary arm 140. That is, X-ray source part driving means 115 is mounted at a part where the rotary arm 140 and the X-ray source part 110 are connected with each other, so that the X-ray source part 110 can be moved. Therefore, the X-ray source part 110 can be horizontally moved in a direction to get near to the X-ray sensor part 120 or in a direction to get away from the X-ray sensor part 120 without regard to the rotary arm 140. The rotary arm 140 includes mechanical components, such as a control motor, therein necessary for driving the X-ray source part 110. Therefore, the CT photographing or the panoramic photographing can be conducted by varying a distance between the object 130 and the X-ray source part 110 and regulating an enlargement ratio.

Figure 2:
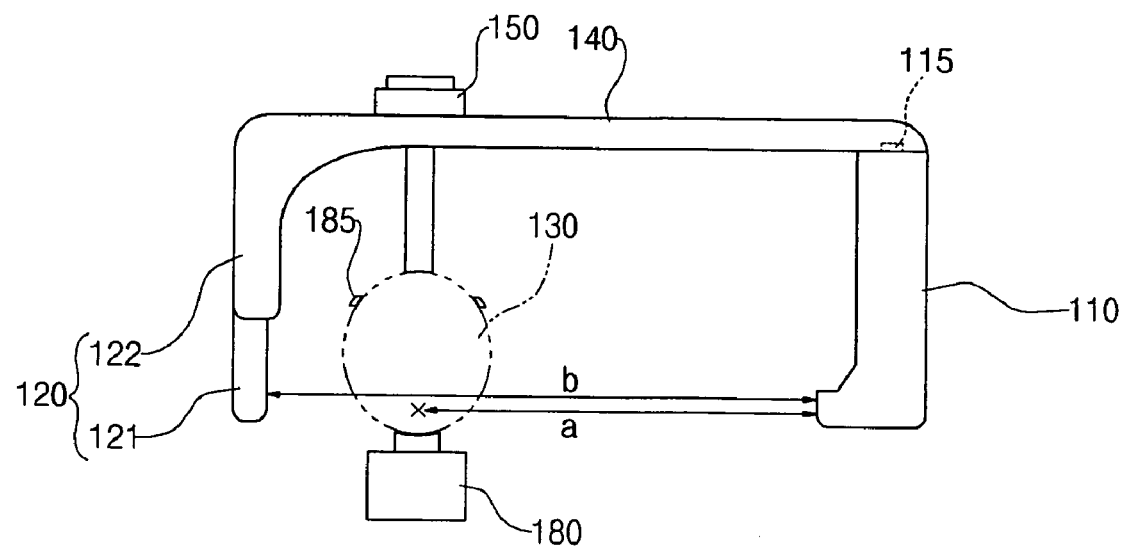
FIGS. 2 to 5 are front views for showing an operation of an X-ray source part of the combined panoramic, computed tomography and cephalometric photographing apparatus according to the first preferred embodiment of the present invention.
Figure 3:
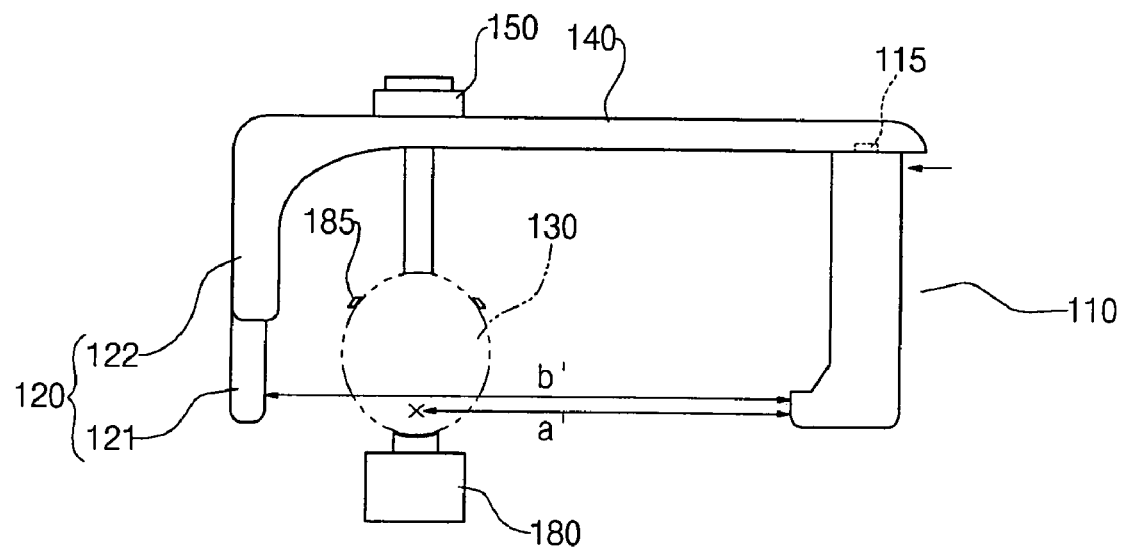
Figure 4:
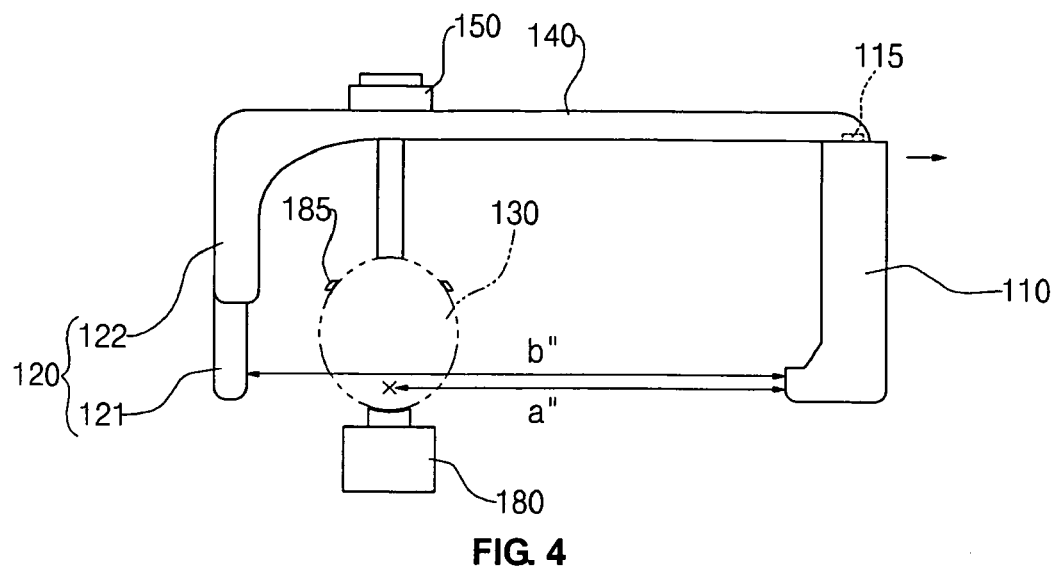

Referring to FIGS. 2 to 4, the operation of the present invention will be described in more detail.

The X-ray sensor part 120 is to convert X-rays into electric signals. The X-ray sensor part 120 detects X-rays generated from the X-ray source part 110, obtains an image, and transmits the obtained image to the outside. The X-ray sensor part 120 is fixed on the rotary arm 140, and includes a sensor mounting part 122 for detaching and attaching a sensor 121. The sensor 121 may be a panoramic sensor or a CT sensor. Therefore, to conduct the CT photographing, a user selects the CT sensor and mounts the CT sensor onto the sensor mounting part 122 manually. To conduct the panoramic photographing, the user separates the CT sensor from the sensor mounting part 122 and mounts the panoramic sensor onto the sensor mounting part 122 manually. That is, in the present invention, the CT sensor for dedicated use of the CT photographing and the panoramic sensor for dedicated use of the panoramic photographing are used according to their use purpose.

It would be appreciated that the sensor mounting part 122 may have one of various shapes besides a slot form shown in the drawings.

Second head fixing means 185 is located between the X-ray source part 110 and the X-ray sensor part 120. The second head fixing means 185 is in the form of a hair band for surrounding the forehead part of the object (patient) 130, and fixes the head part of the patient. That is, the second head fixing means 185 serves to fix the patient's head part together with the chin supporting member 180. Particularly, in case of the CT photographing, a clear image can be obtained without distortion when the patient's head part is not shaken, and so, the second head fixing means 185 have an important role in the present invention. The second head fixing means 185 is connected to a predetermined portion of the rotary arm supporting member 150 through the rotary arm 140 without being influenced by the driving of the rotary arm 140.

The cephalometric photographing part 100b will be described in detail. A horizontal arm 15 having a cephalometric sensor part 11, a collimator 18 and first heading fixing means 17 is connected to a side of the elevation member 170 by a connection member 16.

The horizontal arm 15 includes the cephalometric sensor part 11 mounted on a side thereof.

The cephalometric sensor part 11 has a cephalometric sensor mounting part 12 on which a cephalometric sensor is attached and detached, so that the cephalometric sensor 13 is attached and detached manually.

The cephalometric sensor 13 may be a line scan sensor such as a single line scan sensor or a multi line scan sensor, and in this case, the panoramic sensor 121 may be used as the cephalometric sensor 13. At this time, the line scan type sensor needs the collimator 14 for converting X-rays into parallel rays. Therefore, the collimator 14 is mounted on the other side of the horizontal arm 15 in such a way as to be opposed to the cephalometric sensor 13.

In the case where the X-ray source part 110, the collimator 14 and the cephalometric sensor part 11 are arranged in a line, the cephalometric photographing can be conducted after the panoramic sensor or the CT sensor 121 is separated from the X-ray sensor mounting part. Furthermore, in the case where the X-ray source part 110, the collimator 14 and the cephalometric sensor part 11 are not arranged in a line, the rotary arm supporting member 150 horizontally moves the X-ray source part 110 in a direction that the rotary arm supporting member 150 is connected to the elevation member 170, and then the cephalometric photographing can be conducted.

The first head fixing means 17 is mounted at a predetermined location of the horizontal arm 15 in order to fix the patient's head part (object) 18.

The cephalometric sensor 13 may be an area sensor besides the line scan sensor. In this case, the cephalometric sensor 13 does not need the cephalometric sensor mounting part 12 and the collimator 14. If the area sensor is used as the cephalometric sensor 13, it is possible to conduct photographing in a one-shot type capable of reducing an exposure rate of X-rays and taking an image of a large area at once. Moreover, the cephalometric sensor 13 can use a film.

Hereinafter, referring to FIGS. 2 to 5, a process to conduct the CT photographing, the panoramic photographing and the cephalometric photographing by varying the distance between the X-ray source part 110 and the X-ray sensor part 120 will be described.

Referring to FIGS. 2 and 3, the patient's head part is located on the chin supporting member 180, and fixed by the head fixing means 185.

On the rotary arm 140 supported by the rotary arm supporting member 150, the X-ray source part 110 and the X-ray sensor part 120 are opposed to each other. At this time, the X-ray sensor part 120 is fixed on the rotary arm 140. However, the X-ray source part 110 is not fixed on the rotary arm 140 but movable by the X-ray source part driving means 115.

First, to conduct the panoramic photographing, the panoramic sensor 121 is mounted on the sensor mounting part 122 disposed on the X-ray sensor part 120. The panoramic sensor 121 may use a line scan sensor such as a single line scan sensor or a multi line scan sensor.

In case of the panoramic photographing, the user sets a rotation axis of the rotary arm 140 after setting the central axis (x) on a predetermined part of the patient's body, and then, rotates the rotary arm 140 along the circumference of the central axis and along the fixed locus of the rotation axis.

At this time, to obtain a clear image, it is preferable to conduct photographing after regulating the obtained image into the optimum enlargement ratio. The enlargement ratio means a ratio of the distance between the object 130 and the X-ray source part 110 to the distance between the X-ray sensor part 120 and the X-ray source part 110, and the obtained image is enlarged when the enlargement ratio is increased. When the enlargement ratio is too large, it is harmful to the patient since an amount of the generated X-rays is increased. On the contrary, when the enlargement ratio is too small, it is difficult to form a mechanical structure. Therefore, it is preferable to conduct photographing after selecting the optimum enlargement ratio in order to make the mechanical structure easy and obtain a good image.

In the present invention, photographing shall be conducted by properly regulating the enlargement ratio. In case of the panoramic photographing, it is preferable that the enlargement ratio is 1:1.1 to 1:1.6. Considering the mechanical aspect and an aspect of the highly clear image, it is the most preferable to conduct the panoramic photographing after setting the enlargement ratio to 1:1.3.

For instance, in the case where a distance (a') between the object 130 and the X-ray source part 110 is 454 mm and a distance (b') between the X-ray sensor part 120 and the X-ray source part 110 is 590 mm, it is preferable that the enlargement ratio is about 1:1.3. That is, the user horizontally moves the X-ray source part 110 in the direction to get near to the X-ray sensor part 120 using the X-ray source part driving means 115, and then, conducts the panoramic photographing.

Referring to FIG. 4, after the panoramic photographing, the CT photographing is conducted. First, the user separates the panoramic sensor 121 from the sensor mounting part 122, and then, exchanges the panoramic sensor 121 with the CT sensor 121.

The CT sensor may be an area sensor such as a single area sensor or a multi area sensor, or a sensor of a sequentially driving type.

The CT photographing is conducted by setting the central axis (X) at a predetermined position of the patient and rotating the rotary arm 140 on the central axis.

At this time, it is preferable that the enlargement ratio is 1:1.3 to 1:2. Particularly, it is preferable that the enlargement ratio is 1:1.6 when the patient's anterior teeth part is took by the CT photographing, but 1:1.5 when the patient's posterior teeth part is took by the CT photographing.

In the case where the patient's anterior teeth part is took by the CT photographing, if a distance (a") between the object 130 and the X-ray source part 110 is 424 mm and a distance (b") between the X-ray sensor part 120 and the X-ray source part 110 is 678, the enlargement ratio is about 1:1.6.

In the case where the patient's posterior teeth part is took by the CT photographing, if the distance (a") between the object 130 and the X-ray source part 110 is 424 mm and the distance (b") between the X-ray sensor part 120 and the X-ray source part 110 is 637 mm, the enlargement ratio is about 1:1.5.

That is, the user can conduct the CT photographing after the X-ray source part 110 is horizontally moved in the direction to get away from the X-ray sensor part 120.

Figure 5:
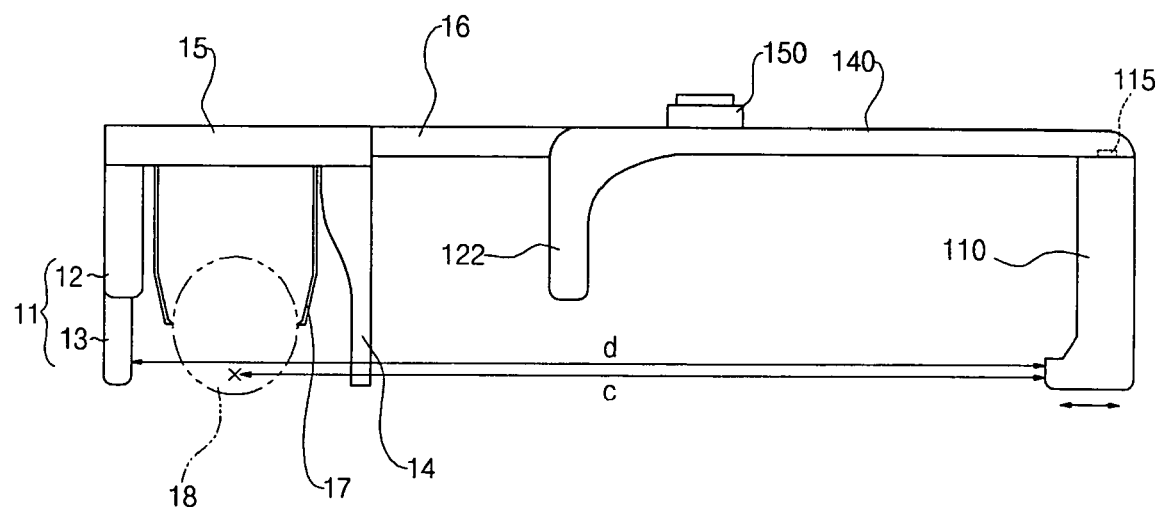

Referring to FIG. 5, after conducting the panoramic photographing and the CT photographing, the cephalometric photographing is conducted.

At this time, in the case where the cephalometric sensor 13 is the line scan sensor and the X-ray source part 110, the collimator 14 and the cephalometric sensor part 11 are arranged in a line, the user separates the CT sensor 121 from the sensor mounting part 122 so as not to detect X-rays generated from the X-ray source part 110 and mounts the panoramic sensor, which has been used for the panoramic photographing, on the cephalometric sensor mounting part 12, and then, conducts the cephalometric photographing. The enlargement ratio is nearly 1:1 which means a distance (c) between the object 18 and the X-ray source part 110 to a distance (d) between the cephalometric sensor part 11 and the X-ray source part 110. If it is necessary to regulate the enlargement ratio at the time of the cephalometric photographing, the X-ray source part 110 is moved and the cephalometric photographing is conducted.

Furthermore, in the case where the X-ray source part 110, the collimator 14 and the cephalometric sensor part 11 are not arranged in a line, there is no need to remove the CT sensor 121. In this case, the X-ray source part 110 is horizontally moved in a direction that the rotary arm supporting member 150 is connected to the elevation member 170 (at right angles to an arrow direction in FIG. 5) without regard to driving of the rotary arm 140, and then, the cephalometric photographing is conducted.

As described above, the combined panoramic, computed tomography and cephalometric photographing apparatus according to the first preferred embodiment of the present invention can conduct all of the CT photographing, the panoramic photographing and the cephalometric photographing, and regulate the enlargement ratio by moving the X-ray source part 110 using the X-ray source part driving means 115.

Mode for Invention

Figure 6:
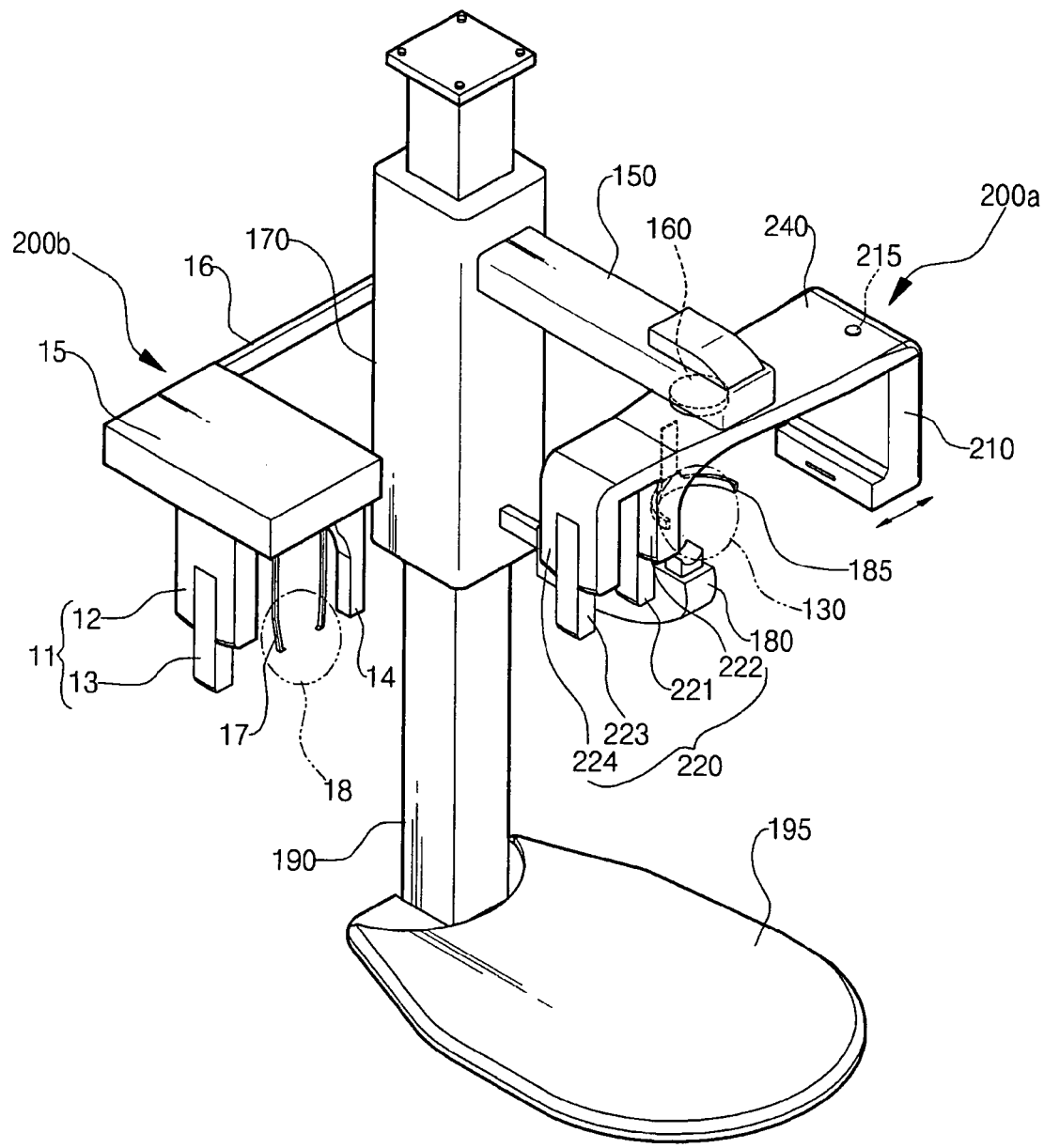
FIG. 6 is a perspective view of a combined panoramic, computed tomography and cephalometric photographing apparatus according to a second preferred embodiment of the present invention.
Figure 7:
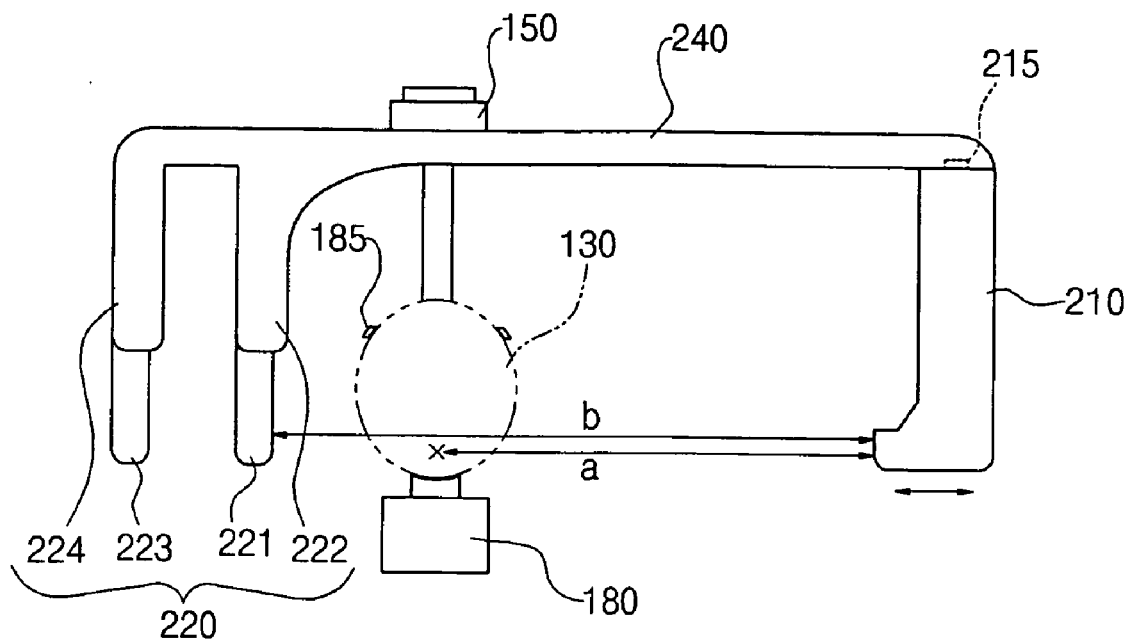
FIGS. 7, 8 and 9 are front views for showing an operation of an X-ray source part of the combined panoramic, computed tomography and cephalometric photographing apparatus according to the second preferred embodiment of the present invention.
Figure 9:
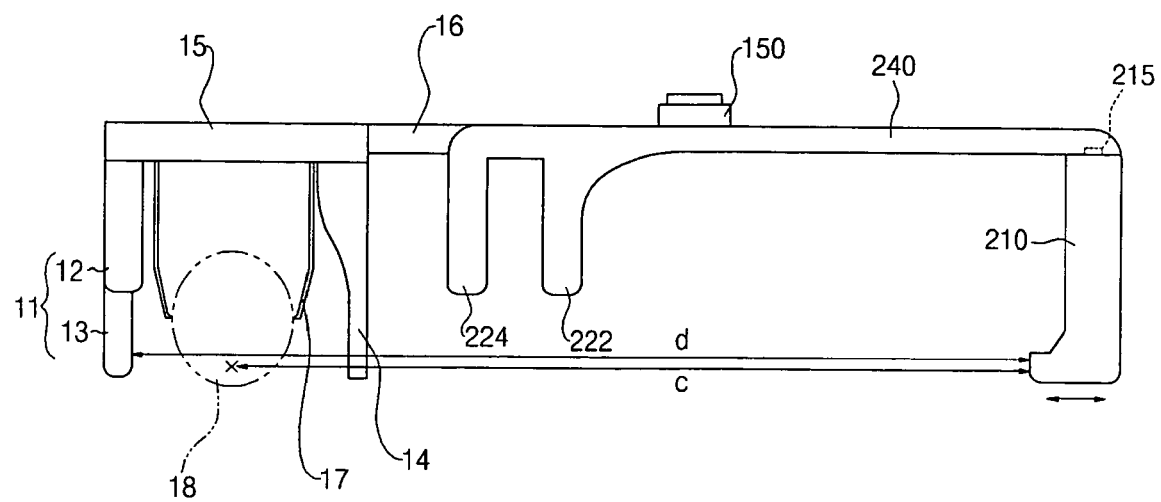

FIG. 6 is a perspective view of a combined panoramic, computed tomography and cephalometric photographing apparatus according to a second preferred embodiment of the present invention, and FIGS. 7 and 9 are front views for showing an operation of an X-ray source part of the combined panoramic, computed tomography and cephalometric photographing apparatus according to the second preferred embodiment of the present invention.

Referring to FIG. 6, the combined panoramic, computed tomography and cephalometric photographing apparatus 200 includes a base 195, a supporting pole 190, an elevation member 170, a panoramic and CT photographing part 200a, and a cephalometric photographing part 200b, and can conduct CT photographing, panoramic photographing, and cephalometric photographing.

The panoramic and CT photographing part 200a is mounted on the front surface of the elevation member 170, and the cephalometric photographing part 200b is connected to a side of the elevation member 170.

The panoramic and CT photographing part 200a will be described in detail. The panoramic and CT photographing part 200a includes: a rotary arm supporting member 150 connected to the front upper portion of the elevation member 170; a rotary arm 240 supported by the rotary arm supporting member 150 and arranging the X-ray source part 210 for generating X-rays and the X-ray sensor part 220 thereon in such a way that the X-ray source part 210 and the X-ray sensor part 220 are opposed to each other; and rotary arm driving means 160 interposed between the rotary arm 240 and the rotary arm supporting member 150 for driving the rotary arm 240.

The X-ray source part 210 is connected to an end of the rotary arm 240, and the X-ray sensor part 220 is connected to the other end of the rotary arm 240. The X-ray sensor part 220 and the X-ray source part 210 are opposed to each other.

The X-ray source part 210 can be driven without regard to the driving of the rotary arm 240. That is, X-ray source part driving means 215 is mounted at a part where the rotary arm 240 and the X-ray source part 210 are connected with each other, so that the X-ray source part 210 can be moved. Therefore, the X-ray source part 210 can be horizontally moved in a direction to get near to the X-ray sensor part 220 or in a direction to get away from the X-ray sensor part 220 without regard to the rotary arm 240.

The X-ray sensor part 220 is fixed on the rotary arm 240 and includes a first sensor mounting part 222 for mounting a panoramic sensor 221 thereon and a second sensor mounting part 224 for mounting a CT sensor 223 thereon. Preferably, the first sensor mounting part 222 is disposed at a portion which is near to the X-ray source part 210, and the second sensor mounting part 224 is disposed at a portion which is away from the X-ray source part 210 in order to regulate the enlargement ratio.

It would be appreciated that the first and second sensor mounting parts 222 and 224 may select one of various forms besides a slot form shown in the drawings.

The second preferred embodiment of the present invention includes the X-ray sensor part 220 having all of the panoramic sensor 221 and the CT sensor 223.

At this time, in the case where the CT photographing is conducted after the panoramic photographing is first conducted, the panoramic sensor 221 is separated from the first sensor mounting part 222 so as not to detect X-rays generated from the X-ray source part 210, and then, the CT photographing is conducted.

In a different way, to conduct the CT photographing, the first sensor mounting part 222 on which the panoramic sensor 221 is mounted may slide in a predetermined direction. That is, the first sensor mounting part 222 can slide in the predetermined direction so as not to detect X-rays generated from the X-ray source part 210. The first sensor mounting part 22 may take the slot form for fitting the panoramic sensor thereinto or a form that the panoramic sensor is mounted thereon.

The cephalometric photographing part 200b will be described in detail. A horizontal arm 15 having a cephalometric sensor part 11, a collimator 18 and first heading fixing means 17 is connected to a side of the elevation member 170 by a connection member 16.

The horizontal arm 15 includes the cephalometric sensor part 11 mounted on a side thereof.

The cephalometric sensor part 11 has a cephalometric sensor mounting part 12 on which a cephalometric sensor is attached and detached, so that the cephalometric sensor 13 is attached and detached manually.

In the case where the X-ray source part 210, the collimator 14 and the cephalometric sensor part 11 are arranged in a line, the cephalometric photographing can be conducted after the panoramic sensor 221 and the CT sensor 223 is removed. Furthermore, in the case where the X-ray source part 210, the collimator 14 and the cephalometric sensor part 11 are not arranged in a line, the X-ray source part 210 is horizontally moved in a direction that the rotary arm supporting member 150 is connected to the elevation member 170, and then the cephalometric photographing can be conducted.

Hereinafter, referring to FIGS. 7 to 9, a process to conduct the CT photographing, the panoramic photographing and the cephalometric photographing by varying the distance between the X-ray source part 210 and the X-ray sensor part 220 will be described.

Referring to FIG. 7, first to conduct the panoramic photographing, the panoramic sensor 221 is mounted on the first sensor mounting part 222 disposed on the X-ray sensor part 220. After that, the user conducts the panoramic photographing after horizontally moving the X-ray source part 210 using the X-ray source part driving means 215. That is, the X-ray source part 210 is horizontally moved in order to regulate the enlargement ratio properly.

Figure 8:
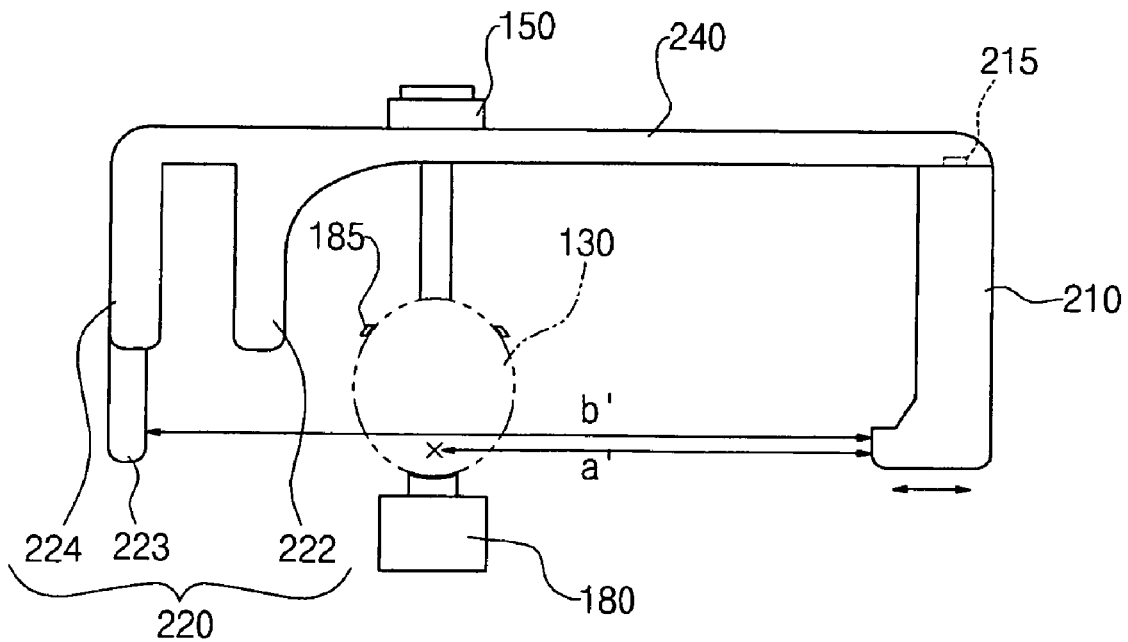

Referring to FIG. 8, to conduct the CT photographing after the panoramic photographing, the user separates the panoramic sensor 221 form the first sensor mounting part 222 or slides the first sensor mounting part 222 in a predetermined direction. After that, the user conducts the panoramic photographing after horizontally moving the X-ray source part 210 in a proper direction using the X-ray source part driving means 215.

At this time, if the locations of the first sensor mounting part 222 and the second sensor mounting part 224 are previously set according to a proper enlargement ratio, the user can conduct the photographing without movement of the X-ray source part 210. However, if a different enlargement ratio is applied, the user can conduct the photographing by moving the X-ray source part 210.

Referring to FIG. 9, after conducting the panoramic photographing and the CT photographing, the cephalometric photographing is conducted.

At this time, in the case where the cephalometric sensor 13 is the line scan sensor and the X-ray source part 210, the collimator 14 and the cephalometric sensor part 11 are arranged in a line, the user separates the panoramic sensor 221 and the CT sensor 223 from the first and second sensor mounting part 222 and 224 and mounts the panoramic sensor 221, which has been used for the panoramic photographing, on the cephalometric sensor mounting part 12, and then, conducts the cephalometric photographing.

Furthermore, in the case where the X-ray source part 210, the collimator 14 and the cephalometric sensor part 11 are not arranged in a line, there is no need to remove the panoramic sensor 221 and the CT sensor 223. In this case, the X-ray source part 210 is horizontally moved in a direction that the rotary arm supporting member 150 is connected to the elevation member 170 (at right angles to an arrow direction in FIG. 9) without regard to driving of the rotary arm 240, and then, the cephalometric photographing is conducted.

As described above, the combined panoramic, computed tomography and cephalometric photographing apparatus according to the second preferred embodiment of the present invention can conduct all of the CT photographing, the panoramic photographing and the cephalometric photographing, and regulate the enlargement ratio by moving the X-ray source part 210 using the X-ray source part driving means 215.

Excepting the above description, the second preferred embodiment of the present invention has the same operation as the combined panoramic, CT and cephalometric photographing apparatus according to the first preferred embodiment.

Figure 10:
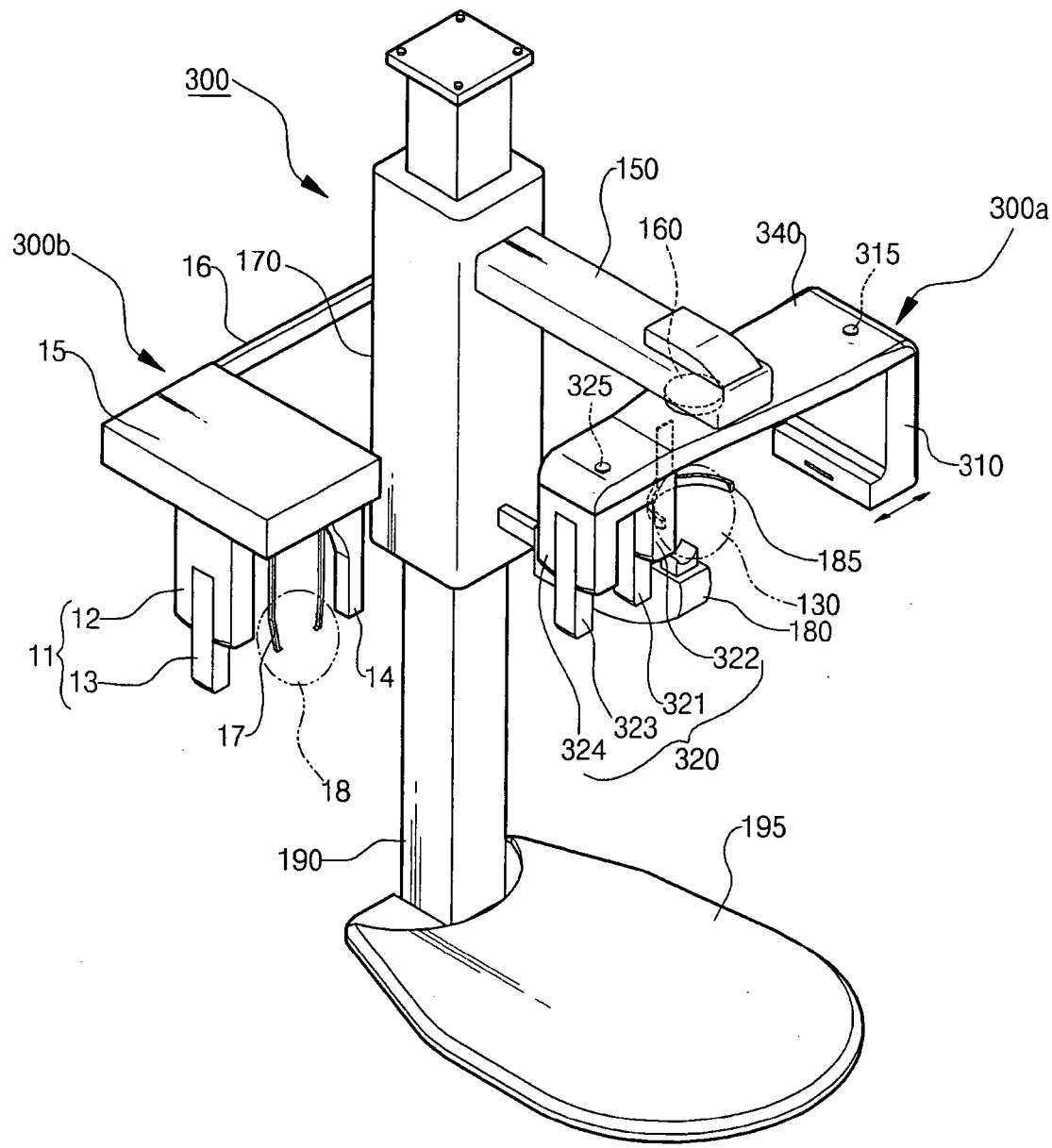
FIG. 10 is a perspective view of a combined panoramic, computed tomography and cephalometric photographing apparatus according to a third preferred embodiment of the present invention.
Figure 11:
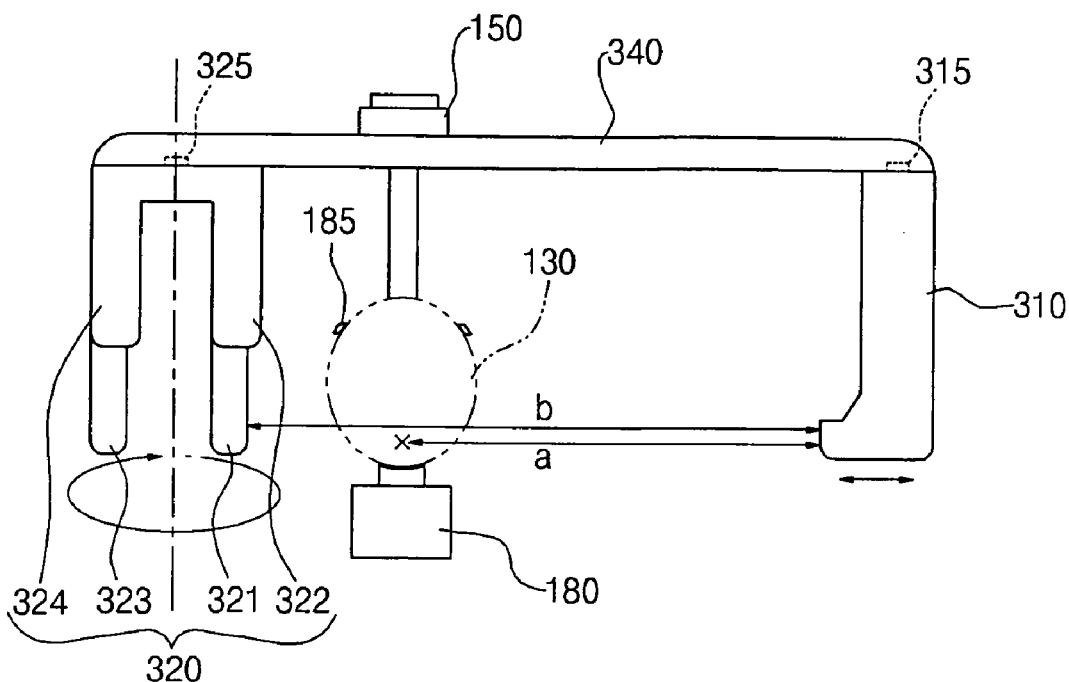
FIGS. 11 and 12 are front views for showing operations of an X-ray source part and an X-ray sensor part of the combined panoramic, computed tomography and cephalometric photographing apparatus according to the first preferred embodiment of the present invention.
Figure 12:
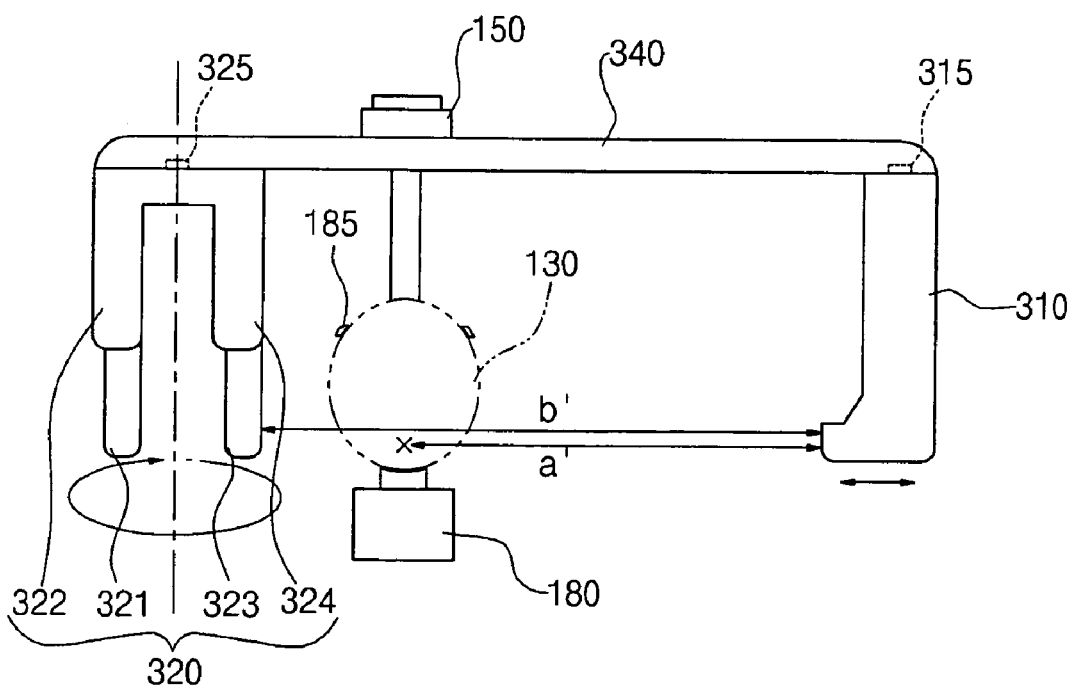

FIG. 10 is a perspective view of a combined panoramic, computed tomography and cephalometric photographing apparatus according to a third preferred embodiment of the present invention, and FIGS. 11 and 12 are front views for showing operations of an X-ray source part and an X-ray sensor part of the combined panoramic, computed tomography and cephalometric photographing apparatus according to the first preferred embodiment of the present invention.

Referring to FIG. 10, the combined panoramic, computed tomography and cephalometric photographing apparatus 300 includes a base 195, a supporting pole 190, an elevation member 170, a panoramic and CT photographing part 300a, and a cephalometric photographing part 300b, and can conduct CT photographing, panoramic photographing, and cephalometric photographing.

The panoramic and CT photographing part 300a is mounted on the front surface of the elevation member 170, and the cephalometric photographing part 300b is connected to a side of the elevation member 170.

The panoramic and CT photographing part 300a will be described in detail. The panoramic and CT photographing part 300a includes: a rotary arm supporting member 150 connected to the front upper portion of the elevation member 170; a rotary arm 340 supported by the rotary arm supporting member 150 and arranging the X-ray source part 310 for generating X-rays and the X-ray sensor part 320 thereon in such a way that the X-ray source part 310 and the X-ray sensor part 320 are opposed to each other; and rotary arm driving means 160 interposed between the rotary arm 340 and the rotary arm supporting member 150 for driving the rotary arm 340.

The X-ray source part 310 is connected to an end of the rotary arm 340, and the X-ray sensor part 320 is connected to the other end of the rotary arm 340. The X-ray sensor part 320 and the X-ray source part 310 are opposed to each other.

The X-ray source part 310 can be driven without regard to the driving of the rotary arm 340. That is, X-ray source part driving means 315 is mounted at a location where the rotary arm 340 and the X-ray source part 310 are connected with each other, so that the X-ray source part 310 can be moved. Therefore, the X-ray source part 310 can be horizontally moved in a direction to get near to the X-ray sensor part 320 or in a direction to get away from the X-ray sensor part 320 without regard to the rotary arm 340.

The X-ray sensor part 320 is not fixed on the rotary arm 340, and rotated without regard to the rotary arm 340. That is, X-ray sensor part driving means 325 is disposed at a location where the rotary arm 340 and the X-ray sensor part 320 are connected with each other, so that the X-ray sensor part 320 can be rotated.

The X-ray sensor part 320 includes a first sensor mounting part 322 for mounting a panoramic sensor 321 thereon and a second sensor mounting part 324 for mounting a CT sensor 323 thereon. Preferably, the first sensor mounting part 322 is disposed at a portion which is near to the X-ray source part 310, and the second sensor mounting part 324 is disposed at a portion which is away from the X-ray source part 310 in order to regulate the enlargement ratio.

The third preferred embodiment of the present invention includes the X-ray sensor part 320 having all of the panoramic sensor 321 and the CT sensor 323, and can drive both of the X-ray source part 310 and the X-ray sensor part 320.

At this time, to conduct the CT photographing after the panoramic photographing, the user rotates the X-ray sensor part 320 to 180° using the X-ray sensor part driving means 325 so that the CT sensor 323 is directly opposed to the X-ray source part 310, and then conducts the CT photographing.

The cephalometric photographing part 300b will be described in detail. A horizontal arm 15 having a cephalometric sensor part 11, a collimator 18 and first heading fixing means 17 is connected to a side of the elevation member 170 by a connection member 16.

The horizontal arm 15 includes the cephalometric sensor part 11 mounted on a side thereof.

The cephalometric sensor part 11 has a cephalometric sensor mounting part 12 on which a cephalometric sensor is attached and detached, so that the cephalometric sensor 13 is attached and detached manually.

In the case where the X-ray source part 310, the collimator 14 and the cephalometric sensor part 11 are arranged in a line, the cephalometric photographing can be conducted after the panoramic sensor 321 or the CT sensor 323 is removed. Furthermore, in the case where the X-ray source part 310, the collimator 14 and the cephalometric sensor part 11 are not arranged in a line, the X-ray source part 310 is horizontally moved in a direction that the rotary arm supporting member 150 is connected to the elevation member 170, and then the cephalometric photographing can be conducted.

Hereinafter, referring to FIGS. 11 to 12, a process to conduct the CT photographing, the panoramic photographing and the cephalometric photographing by varying the distance between the X-ray source part 310 and the X-ray sensor part 320 will be described.

Referring to FIG. 11, first to conduct the panoramic photographing, the panoramic sensor 321 is mounted on the first sensor mounting part 322 disposed on the X-ray sensor part 320. After that, the user conducts the panoramic photographing after horizontally moving the X-ray source part 310 using the X-ray source part driving means 315. That is, the X-ray source part 310 is horizontally moved in order to regulate the enlargement ratio properly.

At this time, to conduct the panoramic photographing after the CT photographing, since the panoramic sensor 321 must be directly opposed to the X-ray source part 310, the X-ray sensor part 320 is rotated to 180° so that the panoramic sensor 321 gets nearer to the X-ray source part 310 than the CT sensor 323.

The X-ray sensor part driving means 325 can rotate the X-ray sensor part 320 on a central axis which is a central point located between the panoramic sensor 321 and the CT sensor 323. When the X-ray sensor part 320 is rotated on the central axis which is the central point located between the panoramic sensor 321 and the CT sensor 323, a distance (b, b') between the panoramic sensor 321 or the CT sensor 323 and the X-ray source part 310 is the same. However, when the X-ray source part 310 is horizontally moved, the user can conduct the photographing while regulating the enlargement ratio differently since the distance can be regulated.

Referring to FIG. 12, to conduct the CT photographing after the panoramic photographing, the X-ray sensor part 320 is rotated on the central axis which is the central point located between the panoramic sensor 321 and the CT sensor 323. That is, the X-ray sensor part 320 is rotated in order to locate the CT sensor 323 nearer to the X-ray source part 310 than the panoramic sensor 321.

Excepting the above description, the third preferred embodiment of the present invention has the same operation as the combined panoramic and CT photographing apparatus according to the first preferred embodiment.

Figure 13:
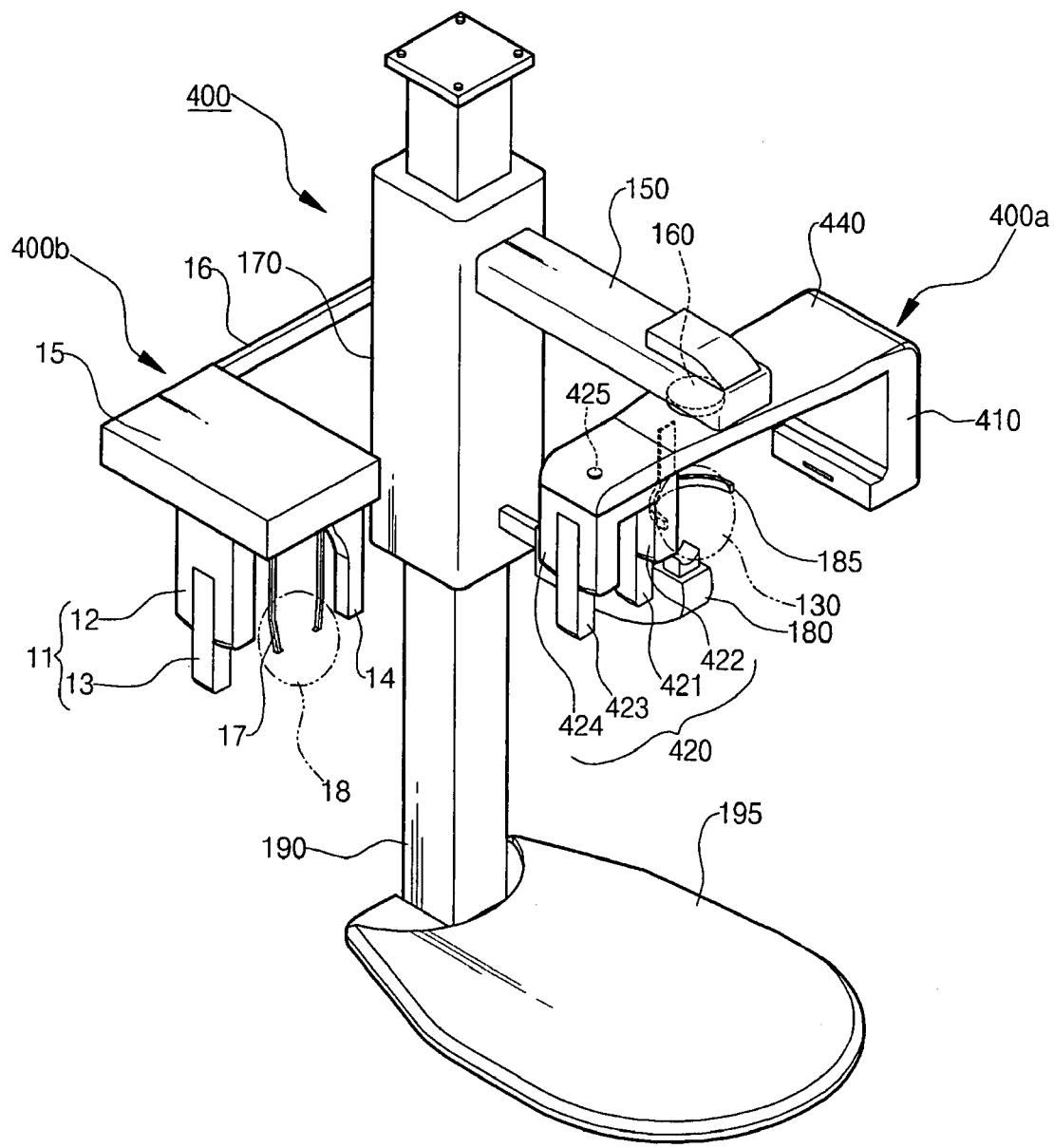
FIG. 13 is a perspective view of a combined panoramic, computed tomography and cephalometric photographing apparatus according to a fourth preferred embodiment of the present invention.
Figure 14:
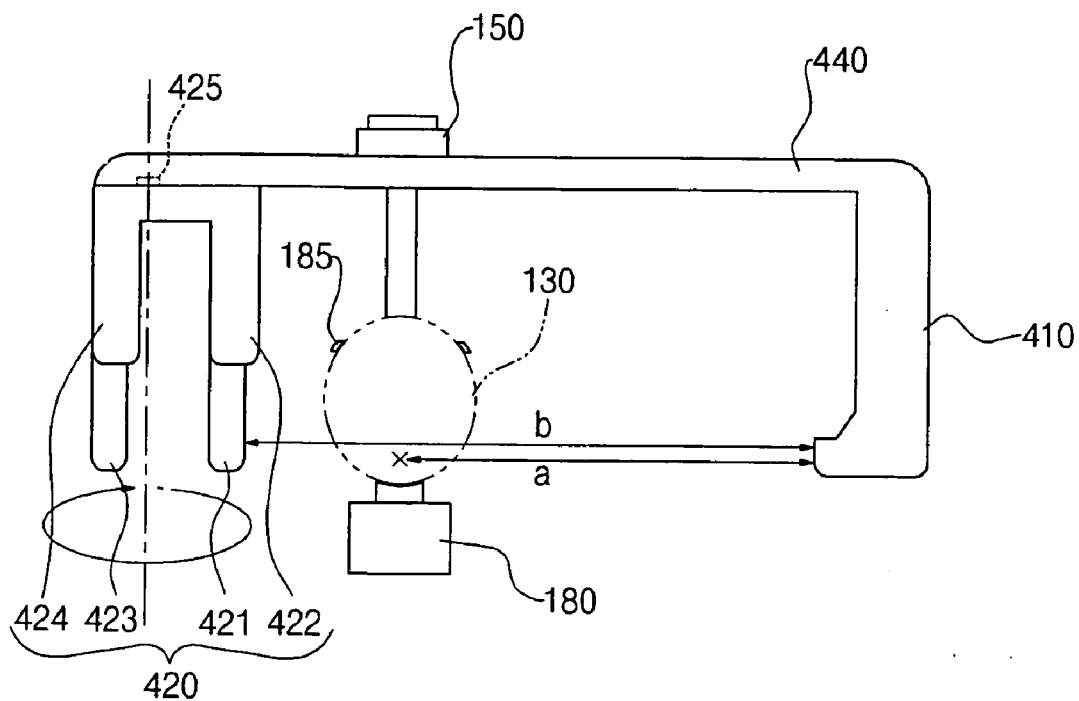
FIGS. 14 and 15 are front views for showing an operation of an X-ray source part of the combined panoramic, computed tomography and cephalometric photographing apparatus according to the fourth preferred embodiment of the present invention.
Figure 15:
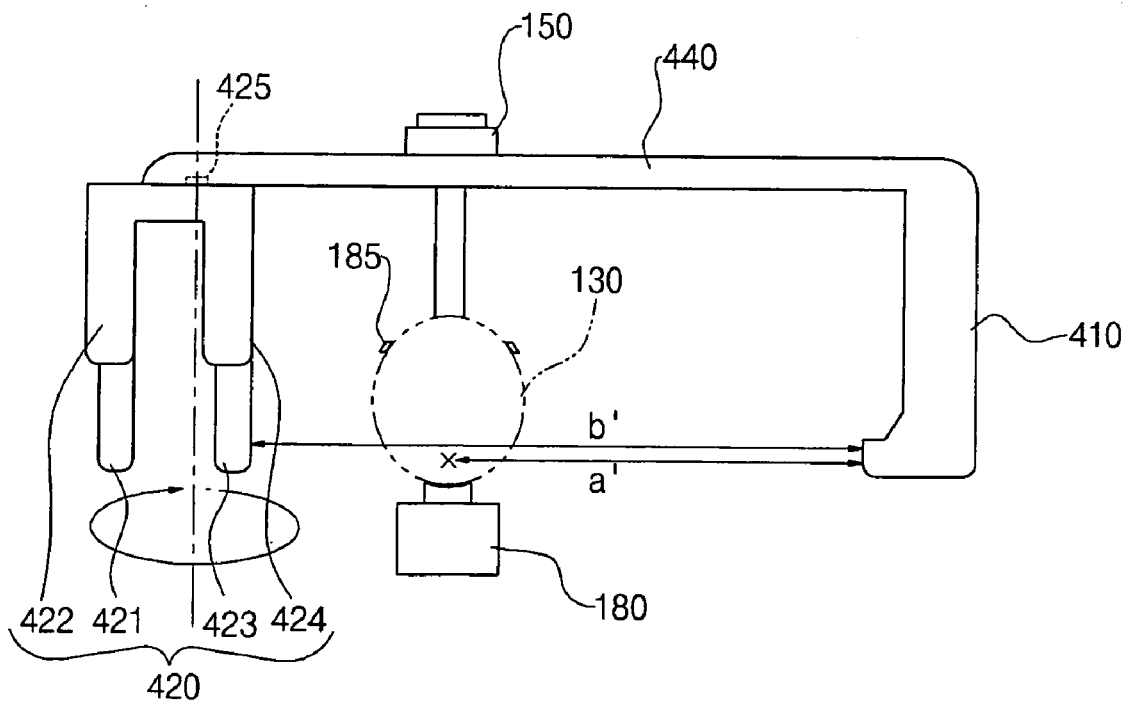

FIG. 13 is a perspective view of a combined panoramic, computed tomography and cephalometric photographing apparatus according to a fourth preferred embodiment of the present invention, and FIGS. 14 and 15 are front views for showing an operation of an X-ray source part of the combined panoramic, computed tomography and cephalometric photographing apparatus according to the fourth preferred embodiment of the present invention.

Referring to FIG. 13, the combined panoramic, computed tomography and cephalometric photographing apparatus 400 includes a base 195, a supporting pole 190, an elevation member 170, a panoramic and CT photographing part 400a, and a cephalometric photographing part 400b, and can conduct CT photographing, panoramic photographing, and cephalometric photographing.

The panoramic and CT photographing part 400a is mounted on the front surface of the elevation member 170, and the cephalometric photographing part 400b is connected to a side of the elevation member 170.

The panoramic and CT photographing part 400a will be described in detail. The panoramic and CT photographing part 400a includes: a rotary arm supporting member 150 connected to the front upper portion of the elevation member 170; a rotary arm 440 supported by the rotary arm supporting member 150 and arranging the X-ray source part 410 for generating X-rays and the X-ray sensor part 420 thereon in such a way that the X-ray source part 410 and the X-ray sensor part 420 are opposed to each other; and rotary arm driving means 160 interposed between the rotary arm 440 and the rotary arm supporting member 150 for driving the rotary arm 440.

The X-ray source part 410 is connected to an end of the rotary arm 440, and the X-ray sensor part 420 is connected to the other end of the rotary arm 440. The X-ray sensor part 420 and the X-ray source part 410 are opposed to each other.

The X-ray source part 410 is fixed on the rotary arm 440. Therefore, the X-ray source part 410 is moved together with the rotary arm 440.

The X-ray sensor part 420 is not fixed on the rotary arm 440, and so, can be driven without regard to the driving of the rotary arm 440. That is, X-ray source part driving means 415 is mounted at a location where the rotary arm 440 and the X-ray sensor part 420 are connected with each other, so that the X-ray sensor part 420 can be moved.

The X-ray sensor part 420 includes a first sensor mounting part 422 for mounting a panoramic sensor 421 thereon and a second sensor mounting part 424 for mounting a CT sensor 423 thereon. Preferably, the first sensor mounting part 422 is disposed at a portion which is near to the X-ray source part 410, and the second sensor mounting part 424 is disposed at a portion which is away from the X-ray source part 410 in order to regulate the enlargement ratio.

The fourth preferred embodiment of the present invention suggests the apparatus including the X-ray sensor part 420 having all of the panoramic sensor 421 and the CT sensor 423, wherein the X-ray source part 410 is fixed on the rotary arm 440 but the X-ray sensor part 420 is movable.

At this time, to conduct the CT photographing after the panoramic photographing, the user rotates the X-ray sensor part 420 to 180° using the X-ray sensor part driving means 425 so that the CT sensor 423 is directly opposed to the X-ray source part 410, and then conducts the CT photographing.

The cephalometric photographing part 400b will be described in detail. A horizontal arm 15 having a cephalometric sensor part 11, a collimator 18 and first heading fixing means 17 is connected to a side of the elevation member 170 by a connection member 16.

The horizontal arm 15 includes the cephalometric sensor part 11 mounted on a side thereof.

The cephalometric sensor part 11 has a cephalometric sensor mounting part 12 on which a cephalometric sensor is attached and detached, so that the cephalometric sensor 13 is attached and detached manually.

In the case where the X-ray source part 410, the collimator 14 and the cephalometric sensor part 11 are arranged in a line, the cephalometric photographing can be conducted after the panoramic sensor 421 or the CT sensor 423 is removed.

Hereinafter, referring to FIGS. 14 and 15, a process to vary the distance between the X-ray source part 410 and the X-ray sensor part 420 and conduct the CT photographing or the panoramic photographing will be described.

Referring to FIG. 14, first to conduct the panoramic photographing, the panoramic sensor 421 is mounted on the first sensor mounting part 422 disposed on the X-ray sensor part 420.

At this time, to conduct the panoramic photographing after the CT photographing, since the panoramic sensor 421 must be directly opposed to the X-ray source part 410, the X-ray sensor part 420 is rotated to 180° so that the panoramic sensor 421 gets nearer to the X-ray source part 410 than the CT sensor 423.

The X-ray source part driving means 415 rotates the X-ray sensor part 420 on an eccentric axis which is located at a predetermined point between the central point between the panoramic sensor 421 and the CT sensor 423 and the CT sensor 423. As described above, in case of the panoramic photographing, it is preferable that the enlargement ratio is 1:1.3, but in case of the CT photographing, it is preferable that the enlargement ratio is 1:1.5 or 1:1.6. Therefore, it is preferable that the X-ray sensor part 420 is rotated on the eccentric axis so that the distance (b) between the panoramic sensor 421 and the X-ray sensor part 410 which are opposed to each other is shorter than the distance (b') between the CT sensor 423 and the X-ray source part 410 which are opposed to each other.

Referring to FIG. 15, to conduct the CT photographing after the panoramic photographing, the X-ray sensor part 420 is rotated on the eccentric shaft which is located at the predetermined point between the central point between the panoramic sensor 421 and the CT sensor 423 and the CT sensor 423. At this time, the distance (b') between the CT sensor 423 and the X-ray source part 410 gets longer than the distance (b)

between the panoramic sensor 421 and the X-ray sensor part 410. The distance (a, a') between the object 130 and the X-ray source part 410 is the same.

To conduct the panoramic photographing again after the CT photographing, the X-ray sensor part 420 is rotated on the eccentric axis to 180° so that the panoramic sensor 421 gets nearer to the X-ray source part 410 than the CT sensor 423.

Excepting the above description, the fourth preferred embodiment of the present invention has the same operation as the combined panoramic, CT and cephalometric photographing apparatus according to the first preferred embodiment.

INDUSTRIAL APPLICABILITY

The combined panoramic, CT and cephalometric photographing apparatus according to the present invention is usable in various fields such as a medical treatment, dental treatment, and so on. The combined panoramic, CT and cephalometric photographing apparatus can obtain the CT image, the panoramic image and the cephalometric image and conduct all of the panoramic photographing, the CT photographing and the cephalometric photographing respectively using the dedicated X-ray sensors for the panoramic photographing, the CT photographing and the cephalometric photographing. Furthermore, the present invention provides the optimum enlargement ratio according to whether the panoramic photographing or the CT photographing is conducted, by regulating the distance between the X-ray source part and the X-ray sensor part, thereby allowing the user to take the image.

The invention claimed is:

1. A combined panoramic, CT (Computed Tomography) and cephalometric photographing apparatus comprising:
   a) a base;
   b) a supporting pole standing on the base;
   c) an elevation member mounted on the supporting pole in such a way as to elevate and displace in a vertical direction;
   d) a panoramic and CT photographing part mounted on the front surface of the elevation member; and
   e) a cephalometric photographing part connected to a side of the elevation member;
      wherein the panoramic and CT photographing part includes:
   1) a rotary arm supporting member connected to the front upper portion of the elevation member;
   2) a rotary arm supported by the rotary arm supporting member and arranging an X-ray source part for generating X-rays and an X-ray sensor part thereon in such a way that the X-ray source part and the X-ray sensor part are opposed to each other, the X-ray sensor part having a panoramic sensor and/or a CT sensor for detecting X-rays which are generated from the X-ray source part and pass through an object;
   3) rotary arm driving means interposed between the rotary arm and the rotary arm supporting member for driving the rotary arm; and
   4) an X-ray source part driving means mounted at a location where the rotary arm and the X-ray source part are connected with each other,
      wherein a distance between the X-ray source part and the X-ray sensor part arranged opposed to each other with respect to the rotary arm is variable,
      wherein the cephalometric photographing part includes:
   i) a cephalometric sensor part for detecting X-rays which are generated from the X-ray source part and pass through the object;
   ii) a horizontal arm for arranging the cephalometric sensor part is mounted at a side thereof; and
   iii) a connection member for connecting the horizontal arm to a side of the elevation member,
      wherein the X-ray sensor part is fixed on the rotary arm, and
      wherein the X-ray source part is horizontally moved in a direction to get near to the X-ray sensor part or in a direction to get away from the X-ray sensor part without regard to the rotary arm,
      wherein the X-ray sensor part includes a sensor mounting part to attach and detach a sensor,
      wherein one of the panoramic sensor and the CT sensor is mounted on the sensor mounting part,
      wherein the X-ray sensor part includes a first sensor mounting part for mounting the panoramic sensor and a second sensor mounting part for mounting the CT sensor.

2. A combined panoramic, CT (Computed Tomography) and cephalometric photographing apparatus according to claim 1, wherein the cephalometric photographing part includes a cephalometric sensor mounting part for attaching and detaching a cephalometric sensor thereon and therefrom.

3. A combined panoramic, CT (Computed Tomography) and cephalometric photographing apparatus according to claim 2, wherein the cephalometric sensor is the same as the panoramic sensor.

4. A combined panoramic, CT (Computed Tomography) and cephalometric photographing apparatus according to claim 3, wherein the panoramic sensor and the cephalometric sensor are line scan sensors.

5. A combined panoramic, CT (Computed Tomography) and cephalometric photographing apparatus according to claim 4, wherein the horizontal arm includes a collimator opposed to the cephalometric sensor part at the other side thereof.

6. A combined panoramic, CT (Computed Tomography) and cephalometric photographing apparatus according to claim 1, wherein the horizontal arm further includes first head fixing means mounted at a predetermined location thereof.

7. A combined panoramic, CT (Computed Tomography) and cephalometric photographing apparatus according to claim 1, wherein the cephalometric sensor is an area sensor.

8. A combined panoramic, CT (Computed Tomography) and cephalometric photographing apparatus according to claim 1, wherein the first sensor mounting part is located near to the X-ray source part, but the second sensor mounting part is located away from the X-ray source part.

9. A combined panoramic, CT (Computed Tomography) and cephalometric photographing apparatus according to claim 8, wherein in case of a CT photographing, the panoramic sensor is separated from the first sensor mounting part so as not to detect X-rays generated from the X-ray source part.

10. A combined panoramic, CT (Computed Tomography) and cephalometric photographing apparatus according to claim 8, wherein in case of the CT photographing, the first sensor mounting part on which the panoramic sensor is mounted slides in a predetermined direction so as not to detect X-rays generated from the X-ray source part.

11. A combined panoramic, CT (Computed Tomography) and cephalometric photographing apparatus according to claim 1, wherein in case of a cephalometric photographing, the X-ray source part is horizontally moved in a direction that the rotary arm supporting member is connected to the elevation member without regard to driving of the rotary arm.

12. A combined panoramic, CT (Computed Tomography) and cephalometric photographing apparatus according to claim 1, further comprising X-ray sensor part driving means located at a location where the rotary arm and the X-ray sensor part are connected with each other.

13. A combined panoramic, CT (Computed Tomography) and cephalometric photographing apparatus according to claim 12, wherein the X-ray sensor part is rotated without regard to the rotary arm, and
wherein the X-ray source part is horizontally moved in a direction to get near to the X-ray sensor part or in a direction to get away from the X-ray sensor part without regard to the rotary arm.

14. A combined panoramic, CT (Computed Tomography) and cephalometric photographing apparatus according to claim 13, wherein the X-ray sensor part includes the first sensor mounting part for mounting the panoramic sensor and the second sensor mounting part for mounting the CT sensor.

15. A combined panoramic, CT (Computed Tomography) and cephalometric photographing apparatus according to claim 14, wherein the X-ray sensor part is rotated on a central axis which is a central point between the panoramic sensor and the CT sensor mounted thereon.

16. A combined panoramic, CT (Computed Tomography) and cephalometric photographing apparatus according to claim 15, wherein in case of the CT photographing, the X-ray sensor part is rotated so that the CT sensor is located nearer to the X-ray source part than the panoramic sensor, and
wherein in case of the panoramic photographing, the X-ray sensor part is rotated so that the panoramic sensor is located nearer to the X-ray source part than the CT sensor.

17. A combined panoramic, CT (Computed Tomography) and cephalometric photographing apparatus according to claim 13, wherein in case of a cephalometric photographing, the X-ray source part is horizontally moved in a direction that the rotary arm supporting member is connected to the elevation member without regard to driving of the rotary arm.

18. A combined panoramic, CT (Computed Tomography) and cephalometric photographing apparatus according to claim 1, further comprising X-ray sensor part driving means mounted at a location where the rotary arm and the X-ray sensor part are connected with each other.

19. A combined panoramic, CT (Computed Tomography) and cephalometric photographing apparatus according to claim 18, wherein the X-ray sensor part is rotated without regard to the rotary arm, and the X-ray source part is fixed on the rotary arm.

20. A combined panoramic, CT (Computed Tomography) and cephalometric photographing apparatus according to claim 19, wherein the X-ray sensor part includes the first sensor mounting part for mounting the panoramic sensor and the second sensor mounting part for mounting the CT sensor.

21. A combined panoramic, CT (Computed Tomography) and cephalometric photographing apparatus according to claim 20, wherein the X-ray sensor part is rotated on an eccentric axis which is located at a predetermined point between a central point between the panoramic sensor and the CT sensor and the CT sensor.

22. A combined panoramic, CT (Computed Tomography) and cephalometric photographing apparatus according to claim 21, wherein in case of the CT photographing, the X-ray sensor part is rotated so that the CT sensor is located nearer to the X-ray source part than the panoramic sensor, and
wherein in case of the panoramic photographing, the X-ray sensor part is rotated so that the panoramic sensor is located nearer to the X-ray source part than the CT sensor.

23. A combined panoramic, CT (Computed Tomography) and cephalometric photographing apparatus according to claim 1, further comprising a rotary arm driving means controller for controlling the rotary arm driving means to move the rotary arm along the fixed locus according to the CT photographing or the panoramic photographing.

24. A combined panoramic, CT (Computed Tomography) and cephalometric photographing apparatus according to claim 1, wherein the CT sensor is an area sensor.

25. A combined panoramic, CT (Computed Tomography) and cephalometric photographing apparatus according to claim 1, further comprising:
a chin supporting member connected to the lower portion of the elevation member; and
second head fixing means located between the X-ray source part and the X-ray sensor part, and connected to a predetermined portion of the rotary arm supporting member.

* * * * *